(12) United States Patent
Walker et al.

(10) Patent No.: US 6,210,681 B1
(45) Date of Patent: Apr. 3, 2001

(54) PLANT PROANTHOCYANIDIN EXTRACTS

(75) Inventors: Edward B. Walker; Richard A. Mickelsen, Jr.; Jennifer N. Mickelsen, all of Ogden, UT (US)

(73) Assignee: JLB, Inc., Ogden, UT (US)

( * ) Notice: Subject to any disclaimer, the term of this patent is extended or adjusted under 35 U.S.C. 154(b) by 0 days.

(21) Appl. No.: 09/391,308

(22) Filed: Sep. 7, 1999

(51) Int. Cl.$^7$ ............................ A01N 65/00; A61K 35/78; A61K 39/385
(52) U.S. Cl. ........................................ 424/195.1; 424/404
(58) Field of Search ................................... 514/456, 724, 514/56; 424/195.1, 404

(56) References Cited

U.S. PATENT DOCUMENTS

| | | |
|---|---|---|
| 3,963,700 | 6/1976 | Philip . |
| 4,083,779 | 4/1978 | Combe et al. . |
| 4,309,207 | 1/1982 | Devlin . |
| 4,652,448 | 3/1987 | Sadowski . |
| 4,775,477 | 10/1988 | Stahl et al. . |
| 4,857,327 | 8/1989 | Virdalm . |
| 5,128,100 | 7/1992 | Hollis et al. . |
| 5,200,186 | 4/1993 | Gabetta et al. . |
| 5,474,774 | 12/1995 | Walker et al. . |
| 5,525,341 * | 6/1996 | Walker et al. ............... 424/195.1 |
| 5,646,178 | 7/1997 | Walker et al. . |
| 5,650,432 | 7/1997 | Walker et al. . |

FOREIGN PATENT DOCUMENTS

| | | | |
|---|---|---|---|
| 1054899 | 10/1991 | (CN) . | |
| 3027933 | 2/1981 | (DE) . | |
| 3427014 | 1/1986 | (DE) . | |
| WO 90/13304 | 11/1990 | (WO) . | |
| WO 92/06695 | 4/1992 | (WO) . | |
| WO 95/26197 | 10/1995 | (WO) . | |
| WO 96/30033 | 10/1996 | (WO) . | |
| WO 99/12541 * | 3/1999 | (WO) ................ | A61K/31/35 |

OTHER PUBLICATIONS

CRC Handbook of Fruit Set and Development: pp. 114, 115 and 117.
Marwan, et al.; "Microbial Inhibitors of Cranberries"; *Journal Food Science;* vol. 51, No. 4; 1986; pp. 1009–1013.
Sobota; "Inhibition of Bacterial Adherence by Cranberry Juice: Potential Use for the Treatment of Urinary Tract Infections"; *The Journal of Urology;* vol. 131; 1984; pps. 1013–1016.
Fuleki, et al.; "Quantitative Methods for Anthocyanins. 1. Extraction and Determination of Total Anthocyanin in Cranberries"; *Journal of Food Science;* vol. 33, 1968; pp. 72–77.
Fuleki, et al.; "Quantitative Methods of Anthocyanins. 3. Purification of Cranberry Anthocyanins"; *Journal of Food Science;* vol. 33; 1968; pp. 266–274.
Ofek, et al.; "Anti–*Escherichia Coli* Adhesion Activity of Cranberry and Blueberry Juices"; vol. 324, No. 22, p. 1599.
Zafriri, et al.; "Inhibitory Activity of Cranberry Juice on Adherence of Type 1 and Type P Fimbriated *Escherichia Coli* to Euracroytic Cells"; *Antimicrobial Agents & Chemotherapy;* vol. 33, No. 1; 1989; pps. 92–98.
Official Methods of Analysis of the Association of Official Analytical Chemists; 1984; pp. 424–425.
Puski, et al.; "Flavonol Glycosides in Cranberries"; *Journal of Food Science;* vol. 32; 1967; pp. 527–530.
The Merck Index, An Encyclopedia of Chemicals, Drugs, and Biologicals; 1989; pp. 291, 452, 453, 640, 857, 941, 999.
Sunset Western Garden Book; 1988; pp. 207, 208, 435 and 436.
Wang, et al.; "Isolation and Characterization of Polyphenolic Compounds in Cranberries"; *Journal of Food Science;* vol. 43. No. 5; 1978; pp. 1402–1404.
Welsh, et al.; "Great Basin Naturalist Memoirs A Utah Flora"; Brigham Young University, Provo, Utah; No. 9; 1987; p. 605.
Letter to the Editor Concerning Antiadhesion in Cranberry and Blueberry—New England Journal of Medicine, vol. 339 (15), 1085–6. Oct. 8, 1998.

* cited by examiner

*Primary Examiner*—Jon P. Weber
*Assistant Examiner*—Patricia D. Patten
(74) *Attorney, Agent, or Firm*—Trask Britt

(57) ABSTRACT

Compounds isolated from plant materials, particularly plants of the genus Vaccinium, which have biological activity measurable as inhibition with adhesion of bacterial cells to surfaces, and an extract of such plant materials which is significantly enriched for the anti-adhesion activity. The specific compounds include procyanidins (also known as "condensed tannins"), leukocyanin and leucodelphinin, and flavonol glucosides including myricetin-3-pyranoside and proanthocyanidin extracts. These proanthocyanidin extracts are capable of inhibiting agglutination reactions of P-type *E. coli*. The extracts containing proanthocyanidins contain at least one A-type interflavanoid bond. Methods of making an extract having the properties. Methods of preventing or treating urogenital infections in a mammal by administering a proanthocyanidin composition including the proanthocyanidin extract, a proanthocyanidin compound, a proanthocyanidin polymer or a mixture thereof, to the mammal in an amount and for a time sufficient to prevent, reduce or eliminate the symptoms associated with such infections and thereby lead to an amelioration or curing of the infection.

11 Claims, 16 Drawing Sheets

| $^{13}C$ NMR (ppm) | Description |
|---|---|
| 158 | |
| 156 | |
| 152 | A-ring C5, C7, C8a |
| 148 | |
| 145 | B-ring C3', C4' Multiplet, 4 or 5 |
| 143 | B-ring C3', C4' Multiplet, 4 or 5 |
| 133 | |
| 129 | B-ring C1' |
| 126 | |
| 121 | B-ring C6' |
| 115 | Multiplet, 3 or 4 |
| 108 | |
| 103 | |
| 100 | 4a |
| 97 | |
| 95 | Unsubstituted A-ring |
| 93 | |
| 84 | |
| 82 | |
| 78 | 2b |
| 73 | |
| 70 | 2c |
| 63 | 3c |
| 60 | |
| 55 | |
| 42 | |
| 39.5 | Multiplet, DMSO |
| 35 | |

Fig. 2

PLANT PROANTHOCYANIDIN EXTRACTS

TECHNICAL FIELD

The invention relates to plant extracts having therapeutic and other uses, and more particularly to extracts of Vitaceae and Ericaceae families.

BACKGROUND

Analysis of the anti-bacterial adhesion fraction of cranberries and other species has been fruitful of late. For instance, the instant inventors, Edward B. Walker, Richard A. Mickelsen, Jr. and Jennifer N. Mickelsen have previously published their findings regarding the active anti-bacterial fraction in U.S. Pat. Nos. 5,525,341, 5,646,178, 5,650,432, and 5,474,774, the contents of all of which are incorporated by this reference in their entirety.

Similarly, later work was evidently conducted at Rutgers University in an attempt to isolate an active fraction of cranberry and other species. See, e.g., Howell et al. "Inhibition of P-fimbriated *Escherichia coli* to Uroepithelial Cell Surfaces by Proanthocyanidin Extracts from Cranberries", *New England Journal of Medicine*, 339(15):1085–6 (Oct. 8, 1998), and International Application No. PCT/US98/18267, published within a year hereof on Mar. 18, 1999.

As described in the foregoing patents and publications, proanthocyanidins are polyphenolic molecules found in fruits, berries and other plant material. These molecules belong to the flavanoid family of compounds. The flavanoid polyphenolics include the catechins, anthocyanins and proanthocyanidins. Proanthocyanidins are also known in the industry as leucoanthocyanins, leucodelphinins, leucocyanins, anthocyanogens, epicatechin-catechin polymers or procyanidins.

DISCLOSURE OF THE INVENTION

The invention includes compounds isolated from plant materials, particularly plants of the genus Vaccinium, which have biological activity measurable as inhibition of adhesion of bacteria to surfaces, and an extract of such plant materials which is significantly enriched for anti-adhesion activity. Other preferred plants include members of the Vitaceae family, particularly of the Vitus genus. The specific compounds include procyanidins (also known as "condensed tannins"), leukocyanin and leucodelphinin, and flavonol glucosides including myricetin-3-pyranoside. An exemplary, preferred procyanidin compound is a substituted epicatechin-catechin dimer.

The present invention is further directed to proanthocyanidin extracts. Specifically, a peak of 95 ppm on a $^{13}$C NMR spectrum is found in these proanthocyanidin compositions which is an inherent characteristic of the Howell compounds illustrating an A type linkage. These extracts may be free of tannins, lipids, carbohydrates, simple sugars, protein and amino acids and organic acids as well as being substantially free of anthocyanins. Additionally, these proanthocyanidin extracts are capable of inhibiting agglutination reactions of P-type *E. coli*. As noted, the proanthocyanidin extracts contain at least one A-type interflavanoid bond.

When the extract is analyzed by reverse-phase HPLC on a C18 lipophilic column, characteristic sets of elution peaks of compounds absorbing at 230 nm, 280 nm and 360 nm are observed. When subjected to further purification, one of the 280 nm-absorbing peaks is found to contain the exemplary procyanidin. The flavonol glucosides are purified from 360 nm-absorbing elution peaks. The pyranoside moiety in these compounds may be glucose, mannose, or a like sugar.

The invention also includes a method of making an extract having the properties outlined in the preceding paragraphs, and a method of inhibiting the adhesion of bacteria to surfaces using the extract.

In another embodiment of the present invention, the extract having the properties previously described, for example, the peak at 95 ppm on the $^{13}$C NMR spectrum, can be used to inhibit P-type *E. coli*, but are incapable of inhibiting agglutination of type 1 *E. coli*.

In another embodiment, the proanthocyanidin composition of the invention can be administered as a pharmaceutical composition. The pharmaceutical composition includes the proanthocyanidin extract and a pharmaceutically acceptable carrier such as lactose, cellulose, or equivalent, or contained within a pharmaceutical dosage such as a capsule or tablet.

Another aspect of the invention relates to methods of preventing or treating urogenital infections in a mammal by administering a proanthocyanidin composition including the proanthocyanidin extract, a proanthocyanidin compound, a proanthocyanidin polymer or a mixture thereof, to the mammal in an amount and for a time sufficient to prevent, reduce or eliminate the symptoms associated with such infections and thereby lead to an amelioration or curing of the infection. Preferably, the mammal undergoing treatment is human, but the method is also applicable to animals, such as mink.

In another embodiment, the proanthocyanidin composition of the invention can be used to reduce the pathogenesis of P-type *E. coli* found in the digestive tracts of animals such as mink and other mammals.

A further aspect of the invention relates to methods of reducing the incidence of infection after surgery, treating topical wounds and acne, and preventing or eliminating oral infections using the proanthocyanidin composition of the invention.

The invention further embraces compositions produced by first extracting non-active compounds from plant materials with, for example, a solvent, leaving a pulp or residue enriched for the anti-adhesion active fraction. This pulp or residue may be further processed by acid solubilization followed by selected steps as described in the preceding paragraphs, to further enrich for the active fraction. (See, e.g., FIG. 1).

The extract's anti-adhesion property is useful in a number of areas, for example, in the cleaning of industrial fermentation equipment, medical and dental instruments, medical dressings, laboratory culture jars, and the like. The extract may further have usefulness to inhibit the adhesion of bacteria to surgical implants, to tooth surfaces and oral cell types found in the mouth, and to cells in the urinary tract of humans and/or animals.

A method of inhibiting the adhesion of bacteria includes the steps of providing the described extract, applying the extract in a suitable medium to a surface having bacteria such as *E. coli* adhered thereto and disengaging the bacteria from the surface. The method is useful to inhibit the adhesion of bacteria to such surfaces as teeth, other bacteria adhered to teeth, to human oral epithelial cells, human epithelial urinary tract cells; and to clean dental implants, bacterial fermentation vats, and the like.

BRIEF DESCRIPTION OF THE DRAWINGS

FIG. 2 is a summary of the $^{13}$C NMR data.

DETAILED DESCRIPTION OF THE ILLUSTRATED EMBODIMENTS

Figure 1:
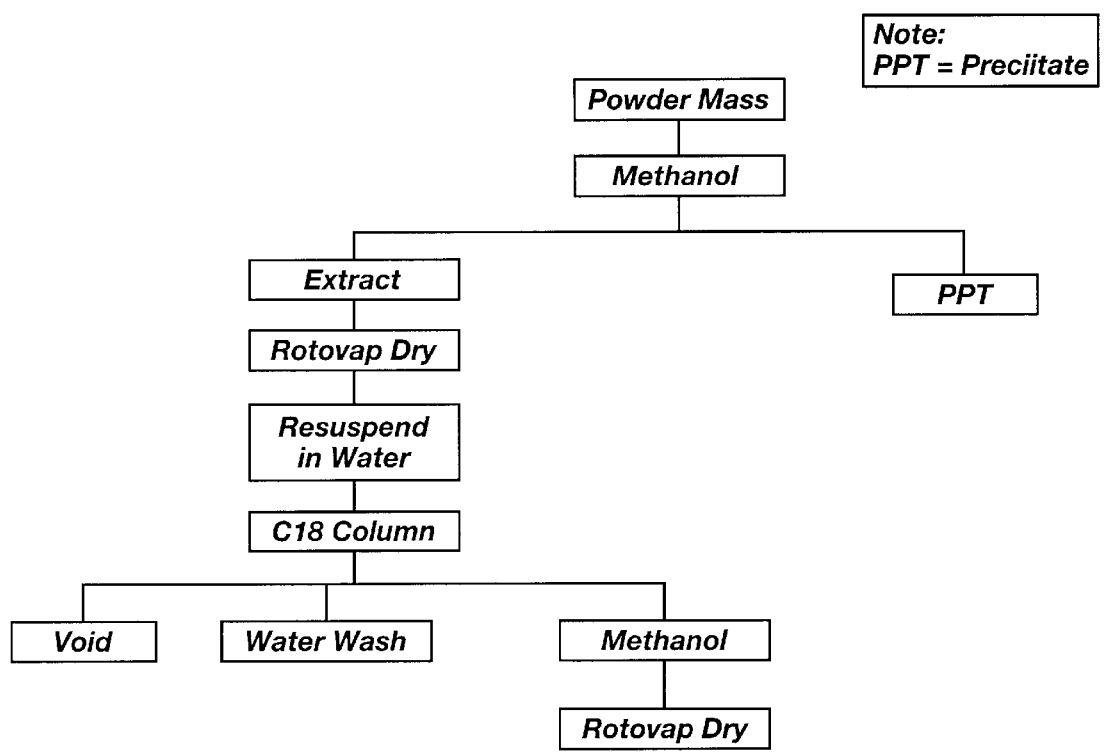
FIG. 1 is a flow chart of an alternate method of extract preparation.
Figure 3A:
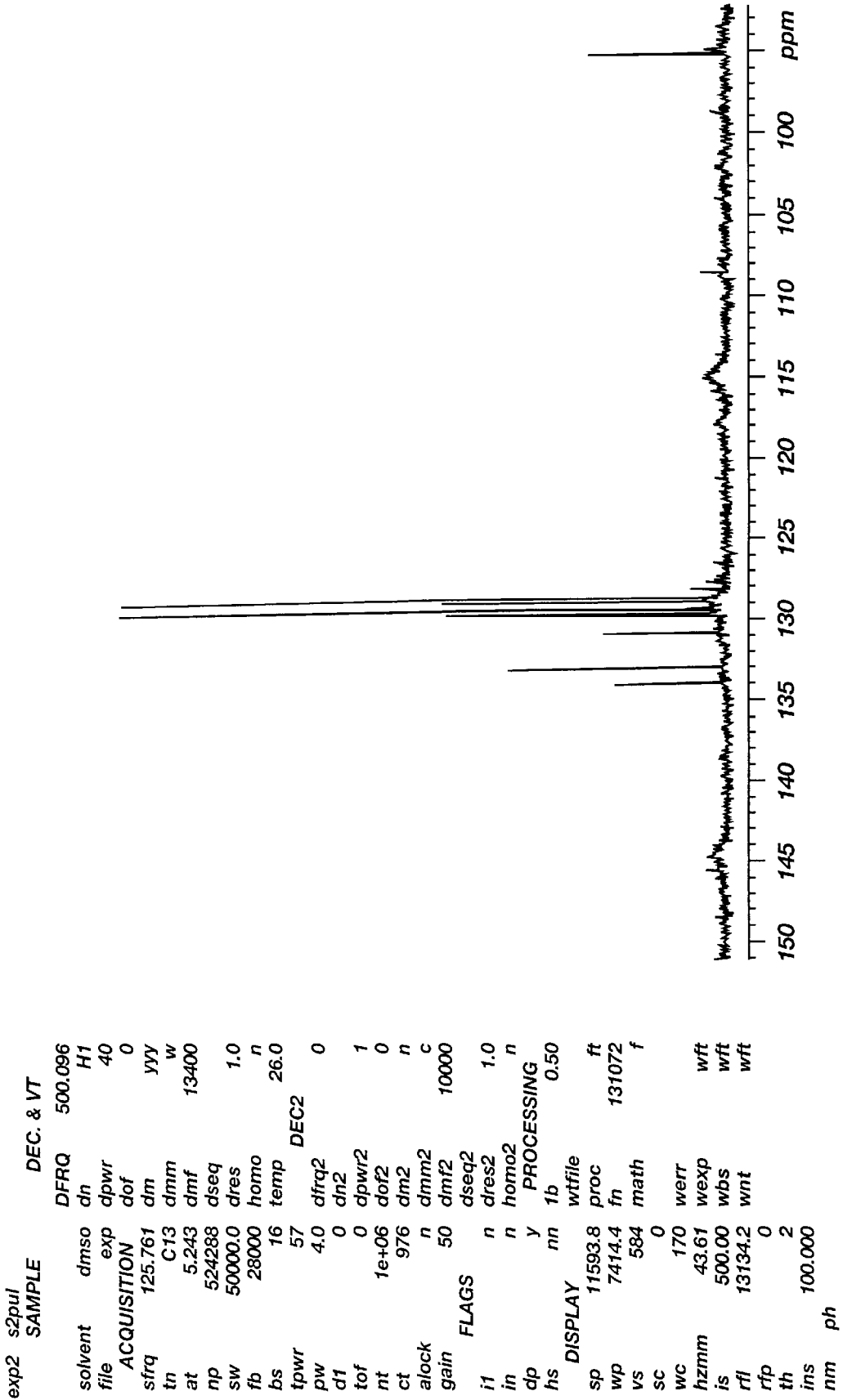
FIG. 3A–3D are charts depicting an $^{13}$C NMR spectrum of the isolated active material isolated as per FIG. 1.
Figure 3B:
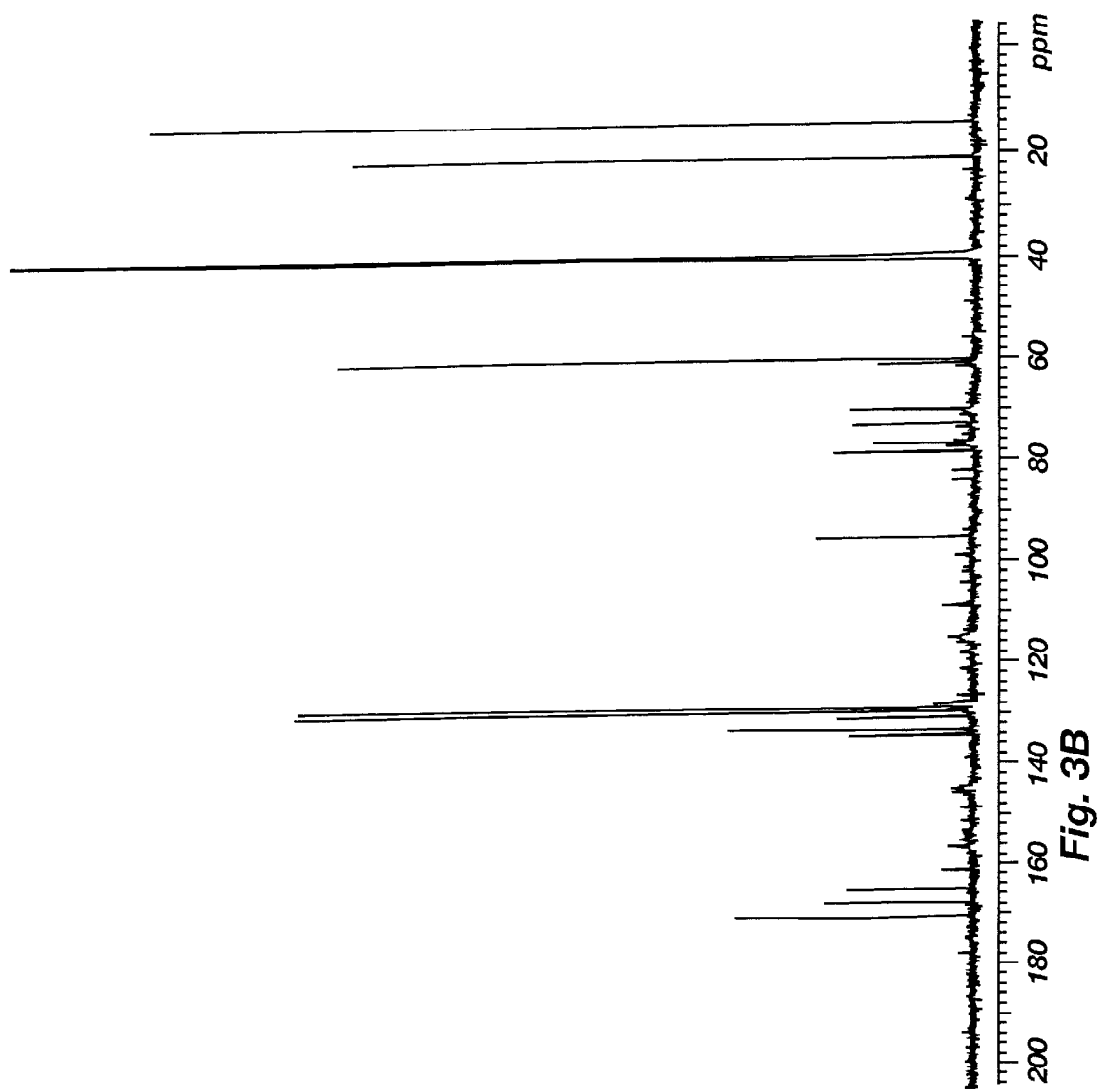
Figure 3C:
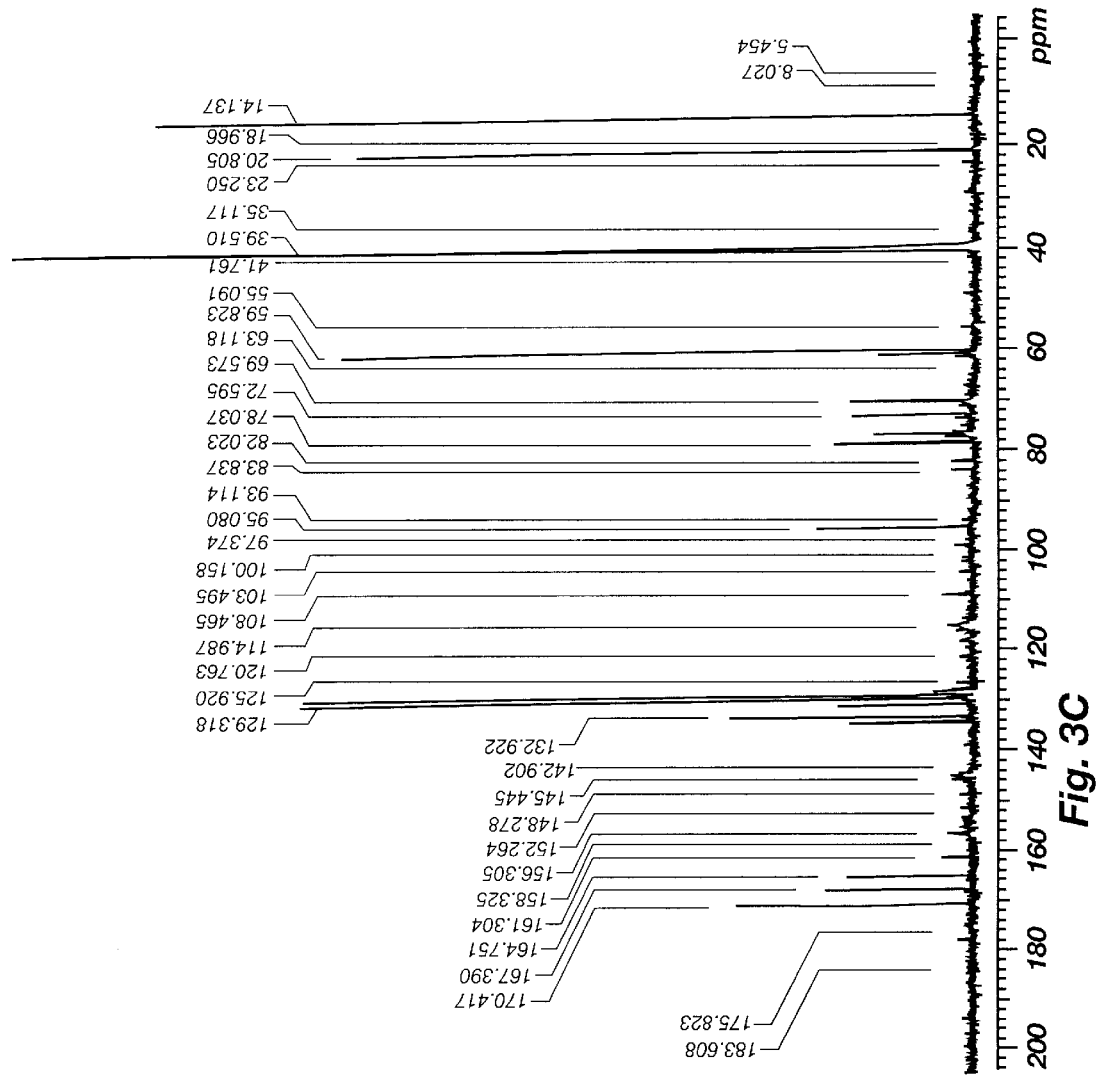
Figure 3D:
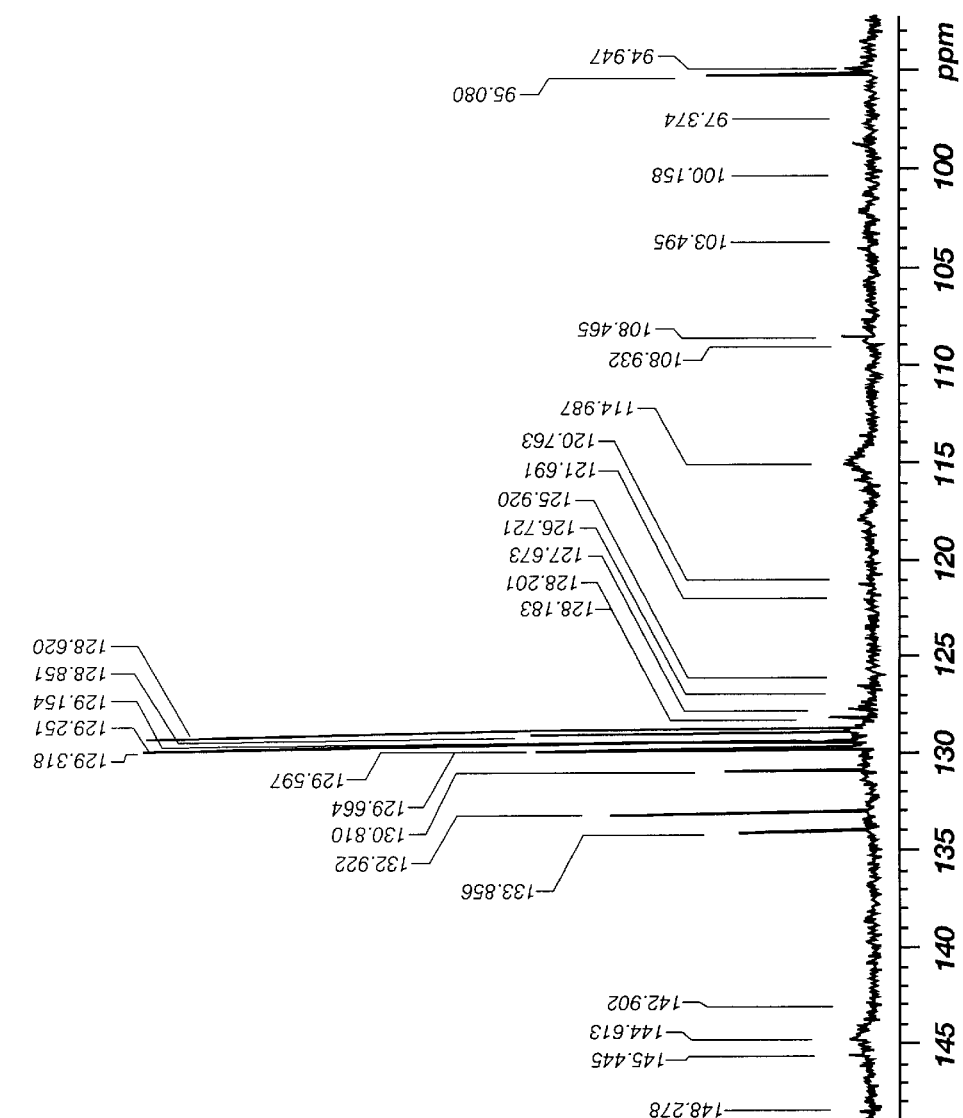
Figure 4A:
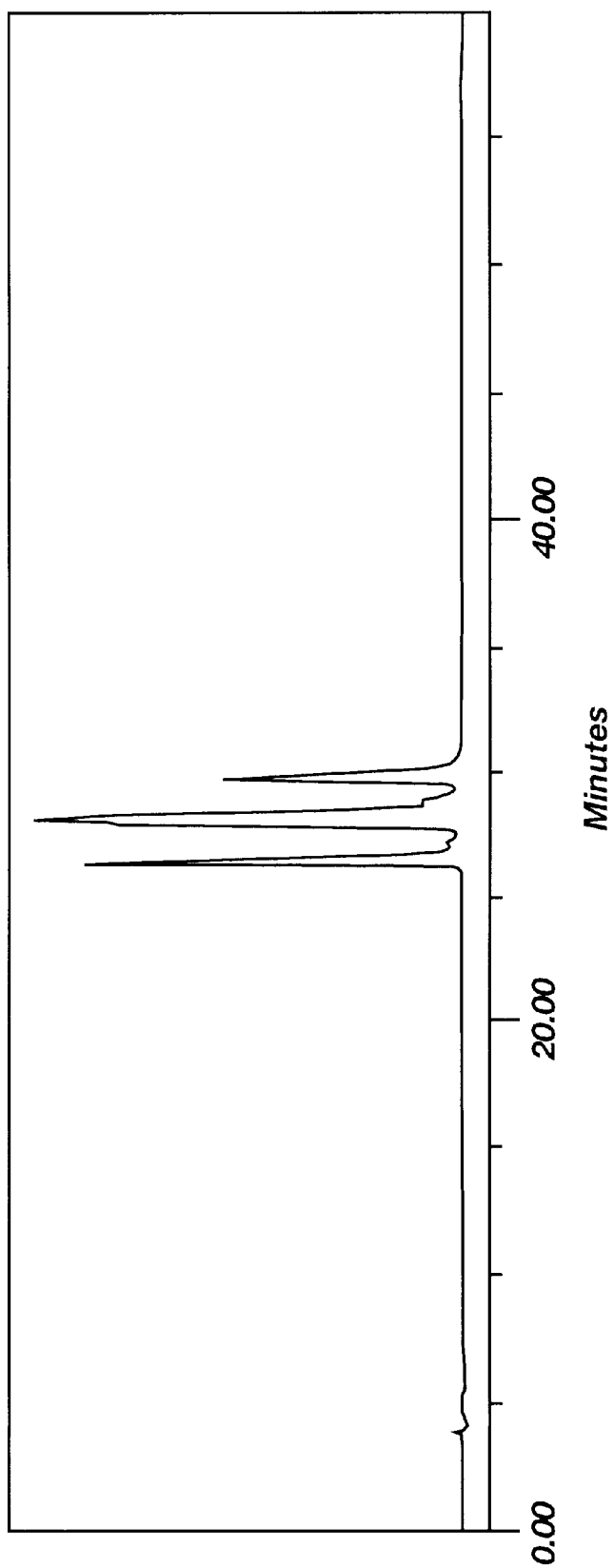
FIG. 4A–4C depict HPLC chromatograms of the products from the selected steps of the process outlined in FIG. 1.
Figure 4B:
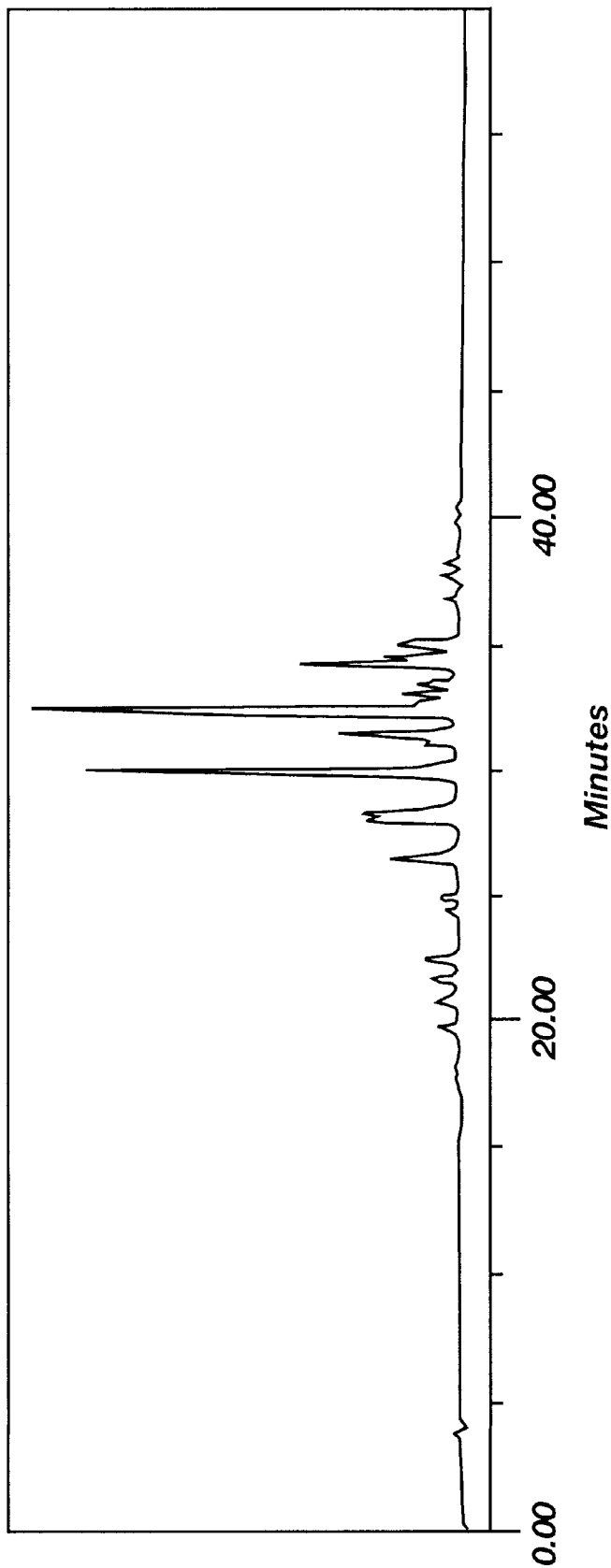
Figure 4C:
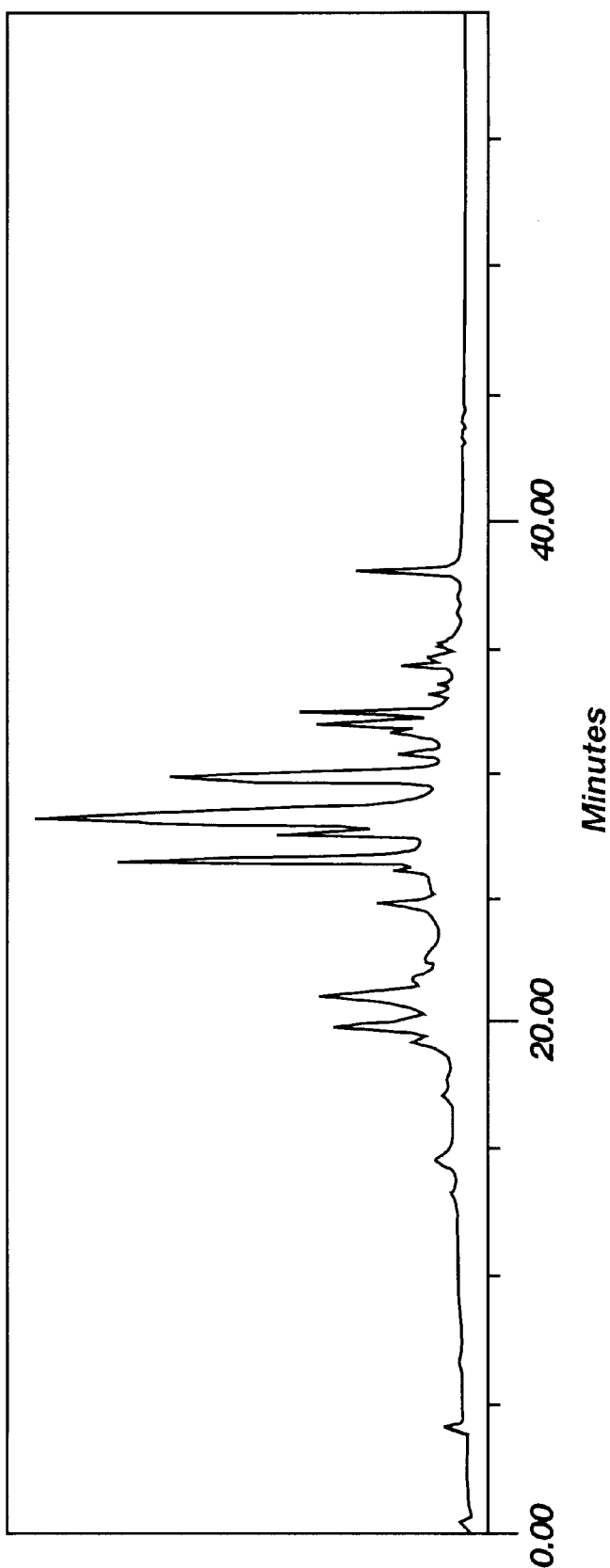
Figure 5:
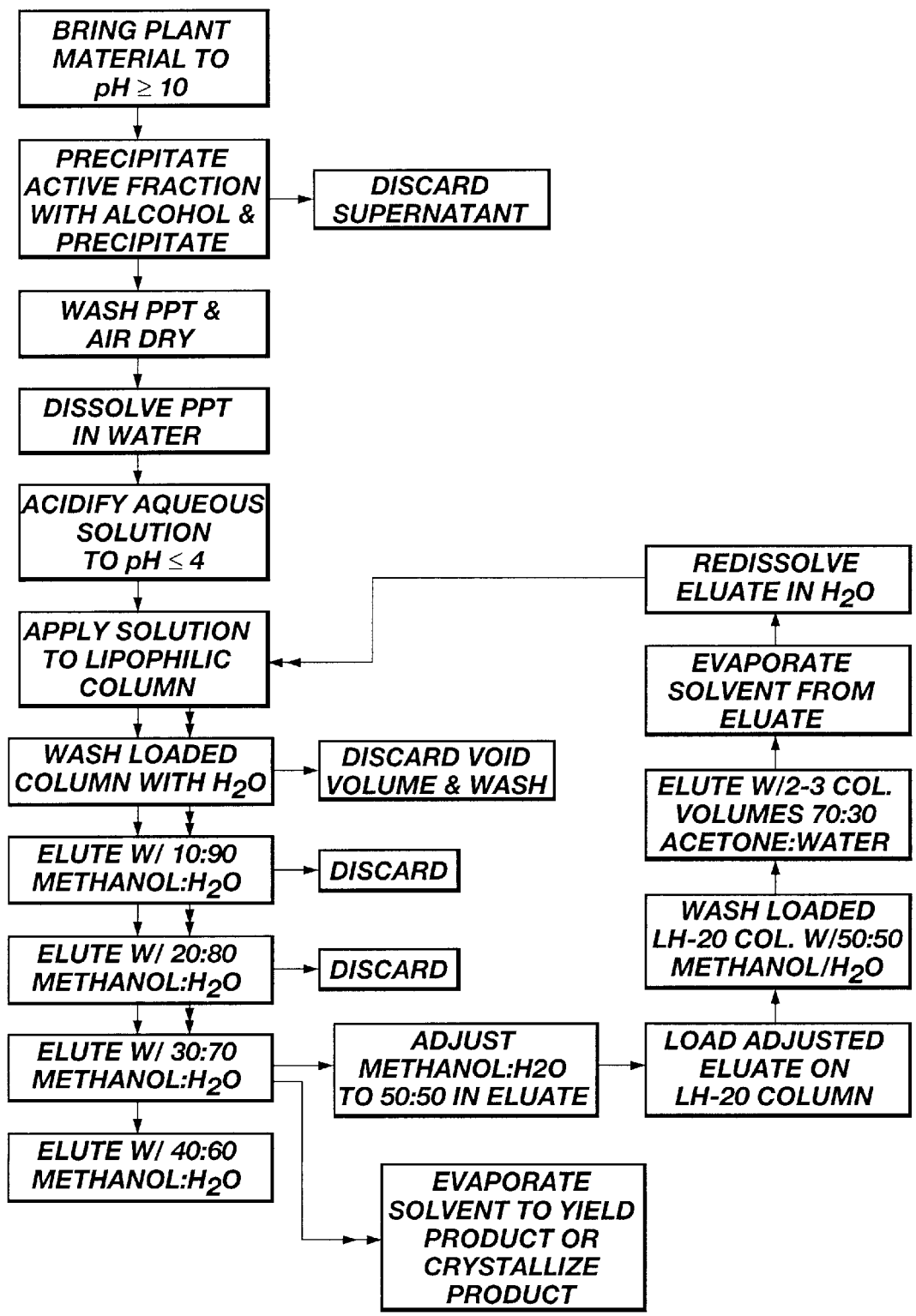
FIG. 5 is a flow chart of an alternate method of extract preparation.

The invention includes an extract of a plant, preferably a species of the genus Vaccinium, which is highly enriched for an active fraction having activity to inhibit the adherence of certain bacterial species to various substrates. Other plants that have demonstrated the ability to inhibit the adherence of certain bacterial species, suitable for use in the present invention, include members of the Vitaceae family. The Vaccinium extract is the preferred embodiment. It may be in powdered form or dissolved in a suitable solvent. The powdered form generally is a reddish powder and other properties as described herein. For convenience and clarity, the extract will be referred to as the "enriched extract," and, when reference is made to an extract made from a particular species such as cranberries, as the "cranberry extract." Additionally, a peak of 95 ppm on a $^3$C NMR spectrum is found in the extract.

In one presently preferred embodiment of the invention, the extract is produced from a powder mass and is then separated using a methanol mix. Any undissolved solids are removed (such as by filtration or centrifugation). The extract polarity is increased by evaporation of organic solvents or by the addition of a polar solvent. Next, the solution is applied to a C18 lipophilic column (Waters SepPak) which has been preconditioned with methanol ("MeOH") followed by deionized water. After the cranberry-derived solution has been loaded into the column, the C18 column is washed with 2 to 3 column volumes of water, and eluted in step-wise fashion with MeOH:H$_2$O mixtures of varying proportions. The solvent is then removed from the extract.

In yet another preferred embodiment, the sample is separated using a water extract. The precipitate is removed and the aqueous layer is placed into a C18 lipophilic column. The void is removed, placed into a rotary evaporator, resuspended and reseparated. The column is then washed with water to remove the sugars. Methanol is added into the column to take out the remaining compounds, which are then placed in a rotary evaporator and reduced before being resuspended in water. The extract is then subjected to a 50:50 chloroform/ethyl acteate mixture before being separated into organic and aqueous layers. Both layers are then separately placed in the rotary evaporator.

A similar embodiment includes separating the extract using methanol and then following the same procedure outlined in the preceding embodiment.

Another embodiment of the invention involves taking the extract of a 10% cranberry solution and applying it to a C18 lipophilic column. The lipophilic column is then washed with water to remove the sugars. Methanol is introduced to removed the active compounds from the lipophilic column. The methanol extract is then centrifuged and/or filtered and the supernatant is placed in a rotary evaporator to dry. The pellet is then resuspended in water and then separated using a 50/50 mixture of chloroform ("CHCL$_3$") with ethyl acetate ("EtOAc"). The organic layer is removed and the aqueous layer is subjected to the rotary evaporator and resuspension in water. The extract is then placed in a cation column to remove the cyanins, where the extract is again placed in a rotary evaporator before being placed in a gel permeation column to determine the molecular weight.

Yet another embodiment uses a method similar to that previously identified. The differences include using the 50:50 chloroform and ethyl acetate separation process at the beginning, before the extract is run through the C18 lipophilic column. The rest of the procedure follows the steps in the aforementioned paragraph.

In another embodiment of the present invention the berries are separated using a solvent selected from the group including: methanol; ethanol; acetone; water; ethyl acetate; PET ether; diethyl ether; n-butanol; methanol: acetic acid ("HOAc"): water; ("MAW"), (10:1:10); ethyl acetate: acetic acid: ETAc: HOAc: ETOH, (10:1:10); ETAc: HOAc: ETOH, (10:1:5); Ethyl ETAc: HOAc: ETOH, (5:1:10); CHCl$_3$: ETAc, (50:50); chloroform: ethyl acetate; CHCl$_3$; acetonitrile; butanol: acenic acid: water, "BAW", (6:1:2); methanol: acetone, (4:1); 5% NH$_3$ in ethanol; 5% NH$_3$ in acetone; 5% NH$_3$ in acetonitrile; amyl alcohol (C$_5$); hexanol (C$_6$); heptanol (C$_7$); 2-octanol (C$_8$); n-decanol (C$_{10}$); acetone: methanol (40:60); methanol with 2% HCl; CHCl$_3$: ETAc (62:38); CHCl$_3$: ETAc (59:41); hydrochloric acid; HCl 3N; hydrochloric acid; HCl 1N; methylene chloride; CH$_2$Cl$_2$; tetra hydrofuran; THF; hexane; potassium hydroxide, "KOH" 6N; sodium hydroxide; 5% NaOH; sodium chloride; 0.85% NaCl; sodium hydroxide; NaOH 1N; p-xylene; toluene; methanol: acetone (50:50).

The precipitate that is separated from the solvent list discussed above is extracted with methanol and separated. The solvent from the first extraction is placed into a rotary evaporator before being resuspended in water. The extract is then placed into a 50/50 mixture of chloroform and ethyl acetate. The aqueous layer that corresponds with the solvent from the first extract is similarly placed in a rotary evaporator to remove the organic solvents. The aqueous layer that corresponds with the solvent from the first extract is then placed in a C18 lipophilic column. The column is washed with sufficient waters before methanol is used to remove the fraction from the column. The fraction containing the extract is then placed in a rotary evaporator before resuspension in water. The extract is then placed in a cation column where it is washed with hydrochloric acid and methanol. The solvent is then removed from the extract.

Yet another embodiment of the present invention includes taking the sample and combining it with one of the solvents mentioned previously to separate the desired extract from the sample. The organic layer is placed in a rotary evaporator and the precipitate and water soluble extract are separated. The aqueous extract is combined with another solvent from the aforementioned list and again separated into organic and aqueous layers. The organic layer is again evaporated and is subjected to the same treatment and the aqueous layer. The extract can be separated continuously using solvents from the aforementioned list.

In a presently preferred embodiment, the concentration of the extract is enriched by at least about 500- to 1500-fold for anti-adhesion activity, as compared with juices which are 100% derived from the plant material. The extract is enriched to a similar degree in the concentration of flavonoid and other polyphenol compounds detected by spectroscopic methods.

In a currently preferred embodiment, the extract is very low in acid and in simple sugars, with a benzoic acid content typically less than about 0.01 milligrams per gram dry powder, and essentially undetectable amounts of free monomer or dimer sugars. The preferred extract is prepared from cranberries (*V. macrocarpon* and variants such as grapes). However, other useful species are *V. myrtilis* (bilberry), *V. oxycoccus* (European cranberry), and *V. corymbosum* (blueberries).

A preferred method of producing the extract includes the steps of preparing a starting extract from plants or plant parts of species selected from the genus Vaccinium (wherein the starting extract includes both charged and polar compounds in the active fraction), concentrating the extract to a smaller volume and enriching the extract for the active fraction, and testing for polyphenol and flavonoid compounds generally. In a preferred embodiment, the method includes the further steps of removing most of the free monomer and dimer sugars from the extract, removing most of the benzoic acid from the extract, and removing anthocyanins. Steps following the preparation of a starting extract, are not necessarily performed in the order listed. Techniques are described for accomplishing each of the indicated steps by chromatography or by precipitation and phase extraction steps. Additionally, in one embodiment, the method includes a step of mannose affinity chromatography which selects for compounds that can compete for binding to a mannose-affinic substrate.

The proanthocyanidin extract can be further fractionated using HPLC or other techniques to identify and characterize specific proanthocyanidin compounds that have anti-adherence activity.against P-type *E. coli* or other microorganisms. Such compounds include 1) proanthocyanidin compounds having an average of at least two to thirty epicatechin flavanoid units, each linked to the next by a B-type interflavanoid bond and 2) proanthocyanidin compounds having an average of one or more epicatechin flavanoid units, i.e., four to seven epicatechin units, each linked to the next by at least one A-type interflavanoid bond.

One procedure for preparing a cranberry extract having anti-adhesion activity which further includes the step of substantially purifying an active compound from the extract, begins with an alkaline pH extraction of the plant material in which the "active" compounds are precipitated. As applied to an aqueous solution of OCEAN SPRAY™ cranberry powder ("OSCP solution"), the method is as follows. A sufficient amount of a strong base (e.g., NaOH) is added to the OSCP solution to bring it to a pH, generally about pH 9 or above, sufficient to ionize phenol groups of polyphenols to phenoxide groups. When the process is applied to the OSCP solution, the solution turns green upon reaching the necessary pH. For 1 liter of a saturated OSCP solution of cranberry powder (20% being generally as much as will dissolve into solution), about 70–80 ml of 10 N NaOH is used. The green, basic OSCP solution thus produced is then stirred with a sufficient amount of a simple alcohol to cause formation of a green precipitate. In the example starting with 1 liter of 20% OSCP, about 4 volumes (e.g., 4 liters) of methanol are used. In place of MeOH, other alcohols miscible with water, including ethanol, isopropanol, butanol, propanol, etc., could be used. The precipitate is allowed to settle, is collected on filter paper, and then is washed with a small volume (about ⅕ to ⅓ liter in the example) of "basic" methanol. The "basic" methanol is alkalinized with about 1–2 ml of 10N NaOH per liter. The washed solids are air dried, and the resulting light green powder, which contains increased levels of the active fraction as revealed by testing in the RBC agglutination assay described herein, is stable for many months at room temperature. Also, most of the sugars are removed in this step. Generally, between about 70 and about 80 grams of green powder are recovered per liter of 20% OSCP.

Next, a sufficient amount of the green powder is dissolved in 200 ml of water to make a strong or nearly saturated solution (generally 30–40 grams for the 20% OSCP process). The aqueous solution is then acidified to convert the phenoxide ions back to phenol groups, in the present case by adding sufficient concentrated acid (about 13–16 ml of 12 M HCl) to bring it to between about pH 3 and about pH 4. In the case of extraction from OSCP, the solution turns to a wine-red color upon reaching the appropriate pH. Any undissolved solids are removed, (e.g., by filtration or centrifugation), and the supernatant solution is applied to a C18 lipophilic column (e.g., Waters SepPak) which has been preconditioned with methanol followed by deionized water. After the cranberry-derived solution has been loaded on to the C18 column, the C18 column is washed with 2–3 column volumes of water, and eluted in step-wise fashion with MeOH:$H_2O$ mixtures of varying proportion. For example, and not by way of limitation, a 35 ml C18 column having about 200 ml of the acidified cranberry-derived solution loaded thereon, can be eluted in a first elution step with 100 ml (2–3 column volumes) of a mixture of 10:90 MeOH/$H_2O$ (vol./vol.), a next elution step with 100 ml of 20:80 MeOH/$H_2O$, a subsequent elution step with 30:70 MeOH/$H_2O$, and a final elution step with 40:60 MeOH/$H_2O$. Other water-miscible alcohols could be substituted for methanol, with appropriate adjustment to the alcohol:water proportions to achieve the desired separation. Also, other organic solvents which are non-polar as compared to water, such as acetonitrile, could be substituted for the alcohol. Further, it is probable that other similar reverse-phase lipophilic columns, such as C2 and C8 columns, could be substituted for the C18 column.

The eluate of the 30:70 wash is highly enriched for anti-adhesion activity, and includes the procyanidin compound. To further purify the procyanidin, the 30:70 wash step eluant is brought to 50% MeOH, either by evaporation and redissolution or by adding MeOH. This solution is then applied to an LH-20 SEPHADEX™ column (available from Sigma Chemicals, of St. Louis, Mo.) which has been preconditioned with 50:50 MeOH/$H_2O$. The column volume should generally be about 1/10 to about ½ of the starting volume of the acidified solution. After loading the 50:50 MeOH-adjusted solution of the eluate on the LH-20 column, the column is washed with 50:50 MeOH/$H_2O$. The LH-20 column is then eluted with about 2–3 column volumes of 70% acetone in water (vol./vol.); the eluate is evaporated to dryness and redissolved in water. The LH-20 column achieves selective separation of catechins, procyanidins polymers, and other polyphenols absorbing at 280 nm, from other polyphenolic compounds. To achieve a similar separation, a phenyl-SEPHAROSE™ column or an LH-60 column (Sigma Chemical Co. of St. Louis, Mo.) could be substituted for the LH-20. Both LH-20 and LH-60 SEPHADEX™ include hydroxypropyl groups pendant via ether linkages from SEPHADEX™ beads, and making the SEPHADEX™ material more lipophilic.

Figure 6A:
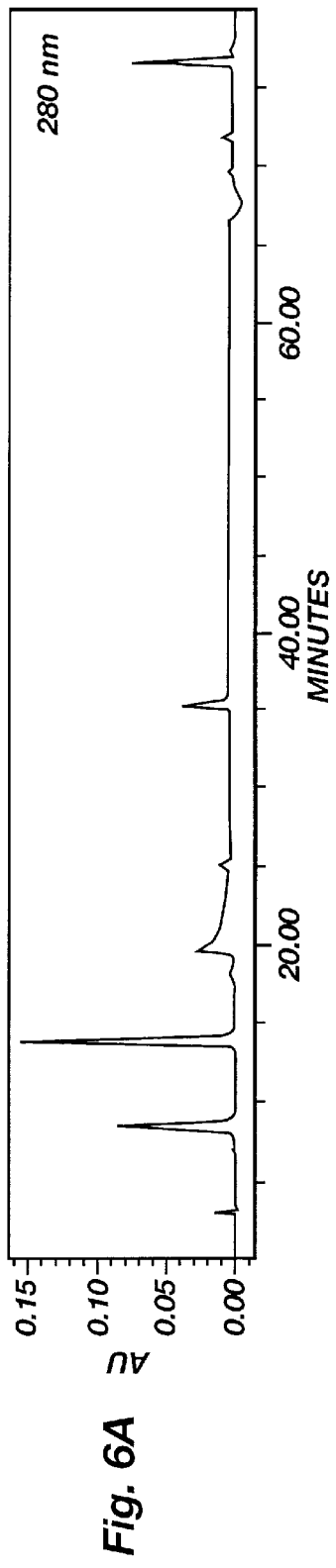
FIG. 6A–6G depict HPLC chromatograms of the products from the selected steps of the process outlined in FIG. 5.

The LH-20 eluate redissolved in water (in neutral form, or preferably acidified), is then applied to another C18 lipophilic column, and subjected to the same step-wise elution protocol. The eluate from the 30% MeOH eluant contains substantially a single compound absorbing at 280 nm, eluting at 18–19 minutes in the analytical HPLC procedure outlined previously herein (FIG. 6D). Generally, between about 0.03 and about 0.10 grams of the purified compound are recovered from 1 liter of the 20% OSCP, that is, a recovery of about 0.01% to about 0.05%. This recovery of a single active compound is at least 20-fold the recovery of mixed active compounds achieved by the methods described previously herein.

Figure 6B:
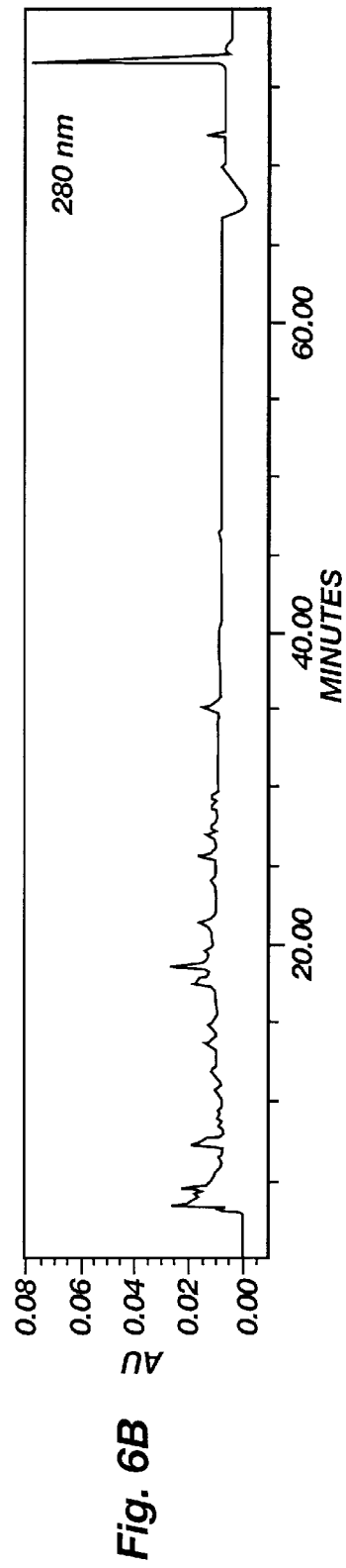
Figure 6C:
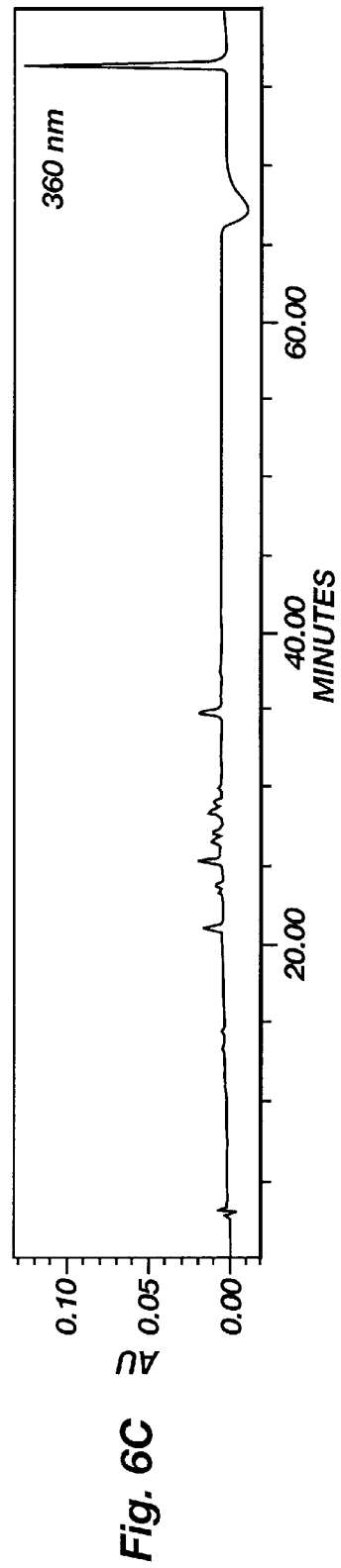
Figure 6D:
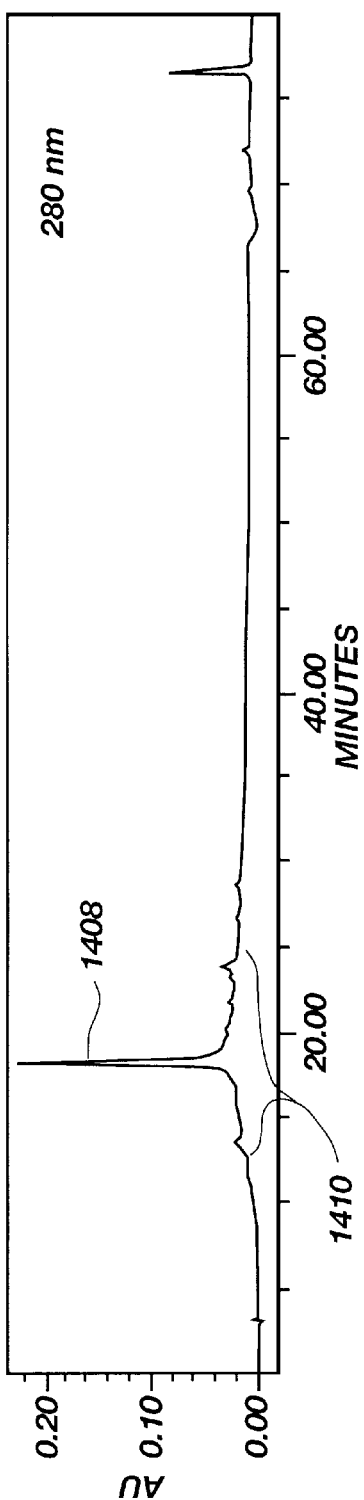
Figure 6E:
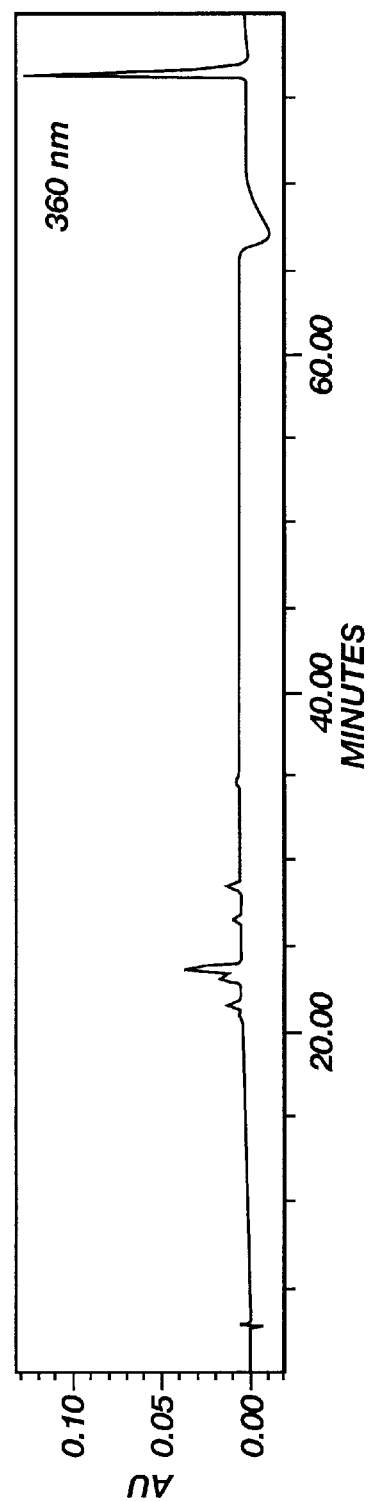
Figure 6F:
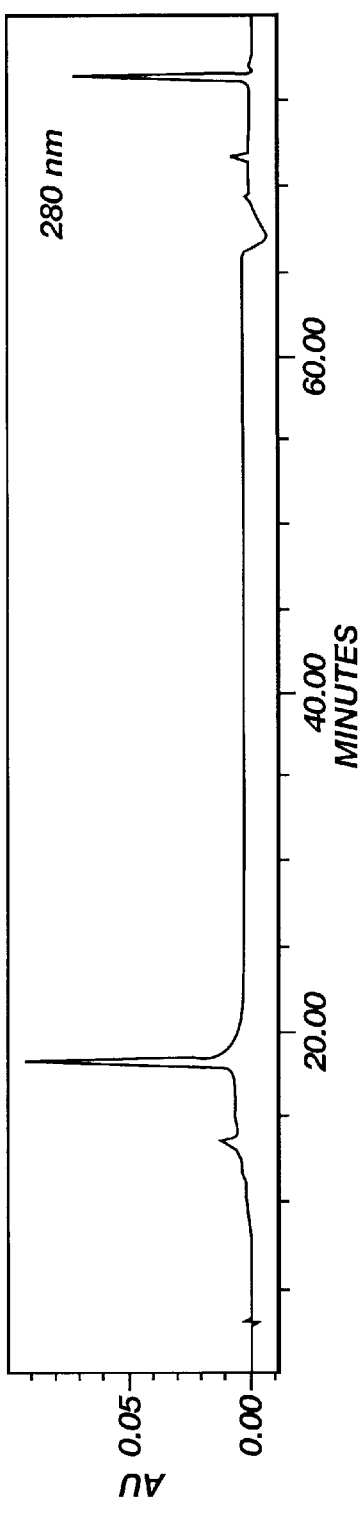
Figure 6G:
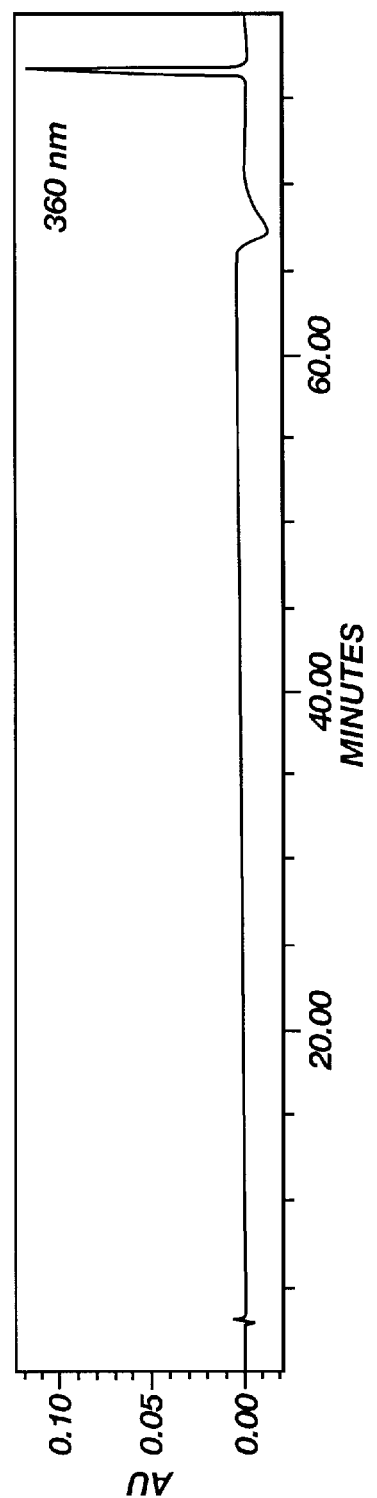

FIGS. 6B–6D depict analytical HPLC chromatograms of products from various steps in the process of FIG. 3. FIG. 6A is an HPLC chromatogram showing the retention time of two marker standards, catechin (peak 1400) and epicatechin (peak 1402), in the same HPLC protocol as FIGS. 6B–D. FIG. 6B is a chromatogram of the product of the eluate after the wash precipitate and air dry, analyzed for compounds absorbing at 280 nm and for compounds absorbing at 360 nm. FIG. 6C shows a chromatogram of the product after the 70:30 wash of acetone:water, also analyzed for compounds absorbing at 280 nm and at 360 nm. FIG. 6D shows a chromatogram of the product of the 20:80 wash methanol:water, from which it is evident that essentially no 360 nm-absorbing compounds remain.

The eluate of the step of the 20:80 wash has been subjected to $^{13}C$ and $^{1}H$ nuclear magnetic resonance ("NMR") analysis, mass spectrometry, and infrared absorbance analysis.

The $^{13}C$ NMR analysis shows an A-type interflavanoid linkage which results when the flavanoid units are joined by two bonds, with one bond occurring between C4 of one unit and C8 of a second unit, while another bond occurs between C2 of one unit and the oxygen attached to C7 of a second unit. Thus, an additional six-membered ring is formed.

One of the embodiments of the present invention provides methods of preventing or treating urogenital infections in a mammal by administering a composition including the proanthocyanidin extract or proanthocyanidin compounds of the invention to the mammal in an amount and for a time sufficient to prevent, reduce or eliminate the symptoms associated with such infection and thereby lead to amelioration or curing of the infection. The composition can also be a pharmaceutical composition or food composition and can be administered for a time an in an amount sufficient to reduce or eliminate the bacteria associated with urogenital infections and thereby ameliorate or cure the infection.

The proanthocyanidins compositions of the invention can be used directly as food additives or mixed with a consumable carrier to be used as a food additive or food composition. One food additive of the invention includes a proanthocyanidin extract of a Vaccinium species and a consumable carrier, wherein the extract is capable of inhibiting agglutination of P-type E. coli. Another food additive of the invention includes one or more proanthocyanidin compounds consisting of an average from at least two to thirty epicatechin flavanoid units, wherein each unit is linked to the next by B-type interflavanoid bonds or proanthocyanidin oligomers as well as eing linked to at least one A-type interflavanoid linkage.

In another embodiment of the present invention, the proanthocyanidins can be mixed in with a consumable food product. This consumable food product can be used as a food composition for livestock or animal feed. The food compositions can be used in a therapeutic fashion to prevent or treat urogenital infections. The food compositions can also be used for beverages, grain products, fruit products and the like. In yet another embodiment, the present invention provides a method of inhibiting adherence of P-type E. coli to a surface which includes placing the bacteria in contact with at least one proanthocyanidin composition, prior to (or concurrently with) allowing the bacteria to contact the surface. The surface may be any substance or material, synthetic or biological, where it is desired to prevent bacterial contamination, accumulation or infection. The surface can also be or constitute a biofilm. In a preferred embodiment, the surface can also be or constitute a biofilm. In a preferred embodiment, the surface is a cellular surface such as an uroepithelial cell surface, cells exposed in a wound or on the skin, a prosthetic device surface, an implant surface or a biofilm.

The proanthocyanidin compositions of the invention can also be used for reducing or treating infection after surgery, treating topical wounds or acne, or preventing or eliminating oral infection by administering a pharmaceutical composition of the invention to a site of infection or potential infection in a patient. The pharmaceutical composition is administered to the patient in accordance with the treatment being rendered. For example, the composition can be applied to a surgical incision or other opening as a liquid, topical cream or by any other suitable delivery means, For topical wounds, the pharmaceutical composition can be a topical cream, salve, dermal antiseptic, dressing (e.g., gauze, tape, etc.) or spray.

Another aspect of the present invention is directed to a method of detecting P-type reactive bacteria in a body fluid sample. This method includes contacting a body fluid sample with a P-type receptor specific assay reagent in an amount to allow for the binding of any P-type reactive bacteria which may be present in the sample to the reagent. The reagent includes a solid-phase substrate coated with one or more proanthocyanidin compositions of the invention. A determination of whether P-type reactive bacteria are present in the sample can be assessed by the degree of agglutination in said sample. The presence of P-type reactive bacteria, especially P-type E. coli, are present if agglutination occurs in the sample.

Another embodiment of the invention provides a test for use in detecting P-type bacteria in a body fluid sample. The test includes of a P-type receptor specific assay reagent which includes a solid-phase substrate coated with one or more proanthocyanidin compositions of the invention. Multiple serial dilutions of the sample or reagent can be used to conduct the assay.

The anti-adhesion activity of proanthocyanidin and proanthocyanidin polymers is believed to be potentiated or otherwise enhanced when combined with a substance selected from the group including Vaccinium-derived flavanols, especially galloyl-substituted tannins including gallocatechin, gallo-epicatechin, and pyranosides of these; Vaccinium-derived leukocyanins, and Vaccinium-derived flavonol pyranosides. Of these, a particularly preferred combination is the proanthocyanidin with the galloyl-substituted tannin, as the latter compounds are believed to inhibit enzymatic degradation of carbohydrate-substituted phenolic compounds. By themselves, the Vaccinium flavanols appear to have little or no anti-adhesion activity. However, at least some Vaccinium-derived flavonol pyranosides do have anti-adhesion activity, although less than the proanthocyanidins.

Of the flavonol pyranosides present in the Vaccinium extract, myricetin-3-pyranoside is one of the most prominent. This compound does have some anti-adhesion activity, but it's anti-adhesion activity is less than that of the proanthocyanidin(s).

At least three modes of bacterial cell adherence to other cells and surfaces are known. One mode is mediated by type 1 pili on the surface of the bacteria, and is characterized by sensitivity to free mannose. A second mode is mediated by P-type pili. The mechanisms of the third mode and other adherence modes, are not well characteried. Guinea pig RBCs are believed to have receptors for the type 1 (mannose-sensitive) pili of E. coli, since the bacteria are capable of agglutinating guinea pig RBCs in the absence of mannose but not in its presence (see for example Aronsen, J. Infect. Dis. 139:329–332, 1979; Riegman, J. Bacter. 172: 1114–1120, 1990; Jann, Infect. Immun. 22:247–254, 1981).

The invention is further explained by use of the following illustrative EXAMPLES.

EXAMPLES

EXAMPLE #1

The strain of E. coli used for the tests on adherence to human bladder

TABLE I

Comparison of HPLC Fractions in
Guinea Pig RBC Agglutination Assay

| Fraction # | Activity Index |
|---|---|
| 510 | 6 |
| 512 | 4 |
| 514 | 5 |
| 516 | 2 |
| 518 | 1 |
| 520 | 0 |
| 522 | 0 |
| 524 | 0 |
| 526 | 4 |
| 504 | 18 |
| 506 | 18 |
| 508 | 6 |
| 500 | 0 |
| 502 | 5 | cell was isolated from an active bladder infection in a human subject. This strain, designated the #3B strain, appears to possess both type 1 and P-type pili (the latter are sometimes referred to in the research literature as "P-type fimbriae").

Results of the agglutination test for various substances and for the two E. coli strains are shown in TABLE II. Gp indicates guinea pig cell assay; HU indicates human cell say. In the guinea pig assay, the highest concentration of final extract in a 25 µl test dot was 0.056 mg/25 µl; the highest amount of anthocyanins in a dot was 0.063 mg/25 µl; the highest amount of mannose was 0.10 mg/25 µl.

TABLE II

Comparison of Adhesion Inhibition by
Extract to that by Known Substances

| Sample ID | Blood | Activity Index |
|---|---|---|
| 1% mannose | Gp | 24 |
| Final Extract | Gp | 10 |
| EXPT. 1 | Hu | 13 |
| Final Extract | Gp | 9 |
| EXPT. 2 | Hu | 11 |
| Alcohol Extract | Gp | 10 |
| Anthocyanins | Hu | 0 |
| Anthocyanins | Gp | 0 |

Results of a similar test performed on a sample of the acidified alcohol extract, with the maximum amount being 0.4 mg/25 µl dot, are also shown. The anthocyanins used in the experiment shown in Table II were obtained from cranberries. The elution of the cation columnm with 1% HCl, after collection of the void volume and aqueous washes, is found to selectively recover much or all of the anthocyanin content of cranberry. The anthocyanin preparation did not contain significant amounts of other substances.

From the results in Tables I and II, it is apparent that the cranberry extract inhibits both type 1 pili-mediated adhesion of E. coli to guinea pig RBCs, and adhesion mediated by P-type pili. Since the extract contains virtually no free monomer or dimer sugars, the inhibition of P-type adhesion cannot be attributed to such sugars. Interestingly, P-type adhesion is believed to occur at high levels in E. coli in urinary tract infections.

The extract also reduced the adherence of Pseudomonas aeruginosa to bladder epithelial cells, although to a lesser degree than observed with E. coli. There was no apparent effect upon the adherence of several Lactobacillus strains to human bladder cells.

Additionally, E. coli did not adhere to polystyrene plastic in the presence of the extract. However, it should be noted that in general E. coli do not tend to greatly adhere to polystyrene.

EXAMPLE #2

A cranberry extract is used as a feed supplement for male mink. During the fall and early winter, male mink have a serious problem with bladder infections. This problem often occurs during the mating season and prevents the male mink from performing. A study was designed in which the mink were feed solid cranberry extract mixed in with their feed every morning. This study illustrated that the cranberry feed additive was helpful in reducing bladder infections in the male mink.

EXAMPLE #3

The invention can also include compounds isolated from plant materials, particularly plants of the family Vitaceae, which have biological activity measurable as inhibition of adhesion of bacteria to surfaces, and an extract of such plant materials which is significantly enriched for anti-adhesion activity. Research has shown that members of the Vitaceae family, particularly of the Vitus genus, inhibit the adhesion of bacteria to surfaces and contain the active ingredients discussed throughout the present application. These extracts can be obtained by processes similar to the methods disclosed herein.

EXAMPLE #4

FIGS. 6B–6G depict analytical HPLC chromatograms of products from various steps in the process of FIG. 1. FIG. 6A is an HPLC chromatogram showing the retention time of two marker standards, catechin (peak 1400) and epicatechin (peak 1402), in the same HPLC protocol as FIGS. 6B–D. FIG. 6B is a chromatogram of the product of washing and air drying the precipitate which was analyzed for compounds absorbing at 280 nm and for compounds absorbing at 360 nm. FIG. 6C shows a chromatogram of the product of the eluate washed in the column with a ratio of 70:30 of acetone: water, also analyzed for compounds absorbing at 280 nm and at 360 nm. FIG. 6D shows a chromatogram of the product of the wash of the eluate of methanol: water at a 20:80 ratio, from which it is evident that essentially no 360 nm-absorbing compounds remain.

The eluate of this step has been subjected to $^{13}C$ and $^{1}H$ nuclear magnetic resonance analysis, mass spectrometry, and infrared absorbance analysis.

Figure 7:
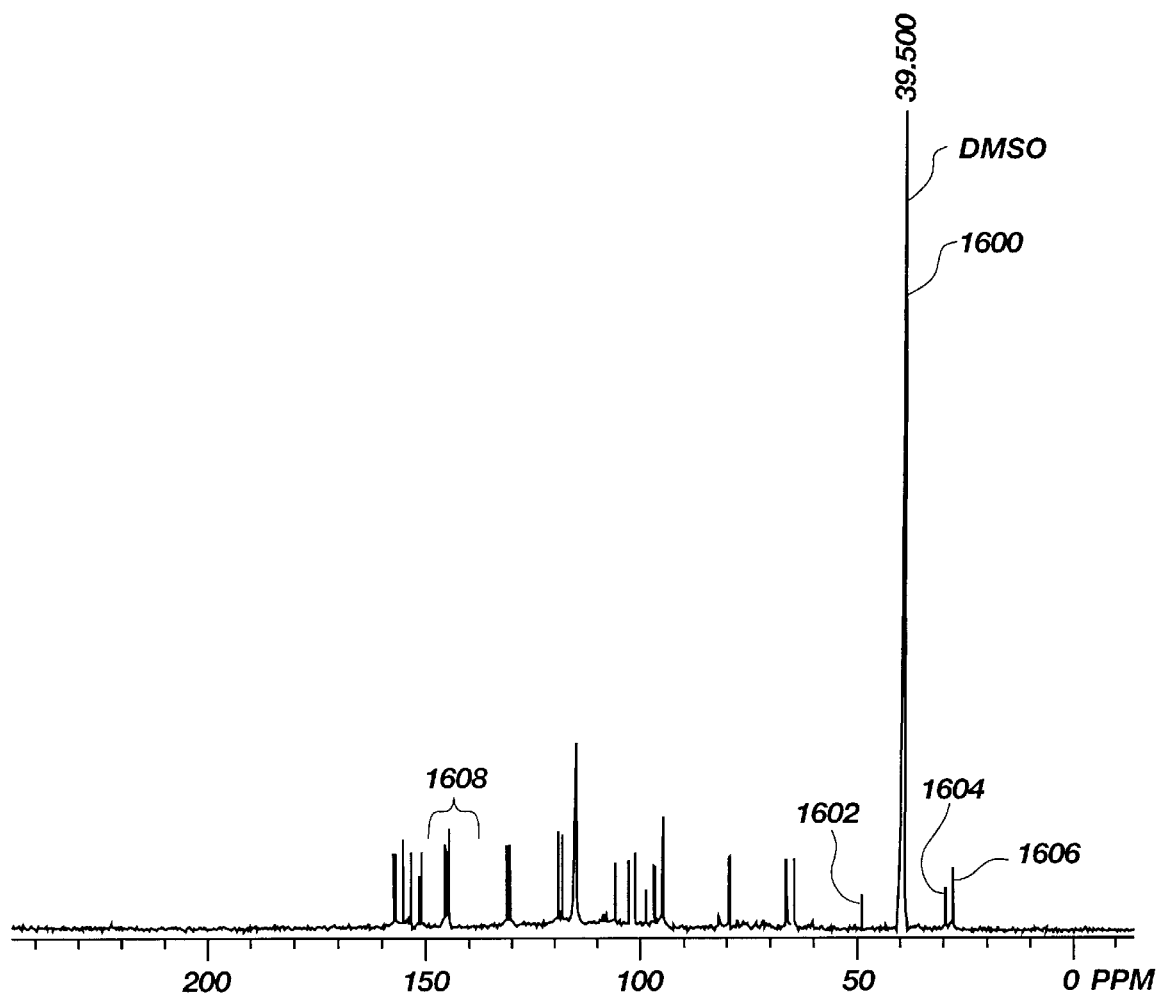
FIG. 7 is a chart depicting an $^3$C NMR spectrum of the isolated active material isolated as per FIG. 5.

FIG. 7 depicts a $^{13}C$-NMR scan of product from step of the 20:80 wash, in $d_6$-dimethylsulfoxide ("DMSO"). Peak 1600 is from the DMSO and methanol solvents. Peak 1604 represents a C4 carbon of an epicatechin ring system, while peak 1606 represents a C4 carbon of a catechin ring system. Peaks 1608 represent the C3 and C4 carbons of a B-ring of a flavanol (catechin) ring system.

Figure 8:
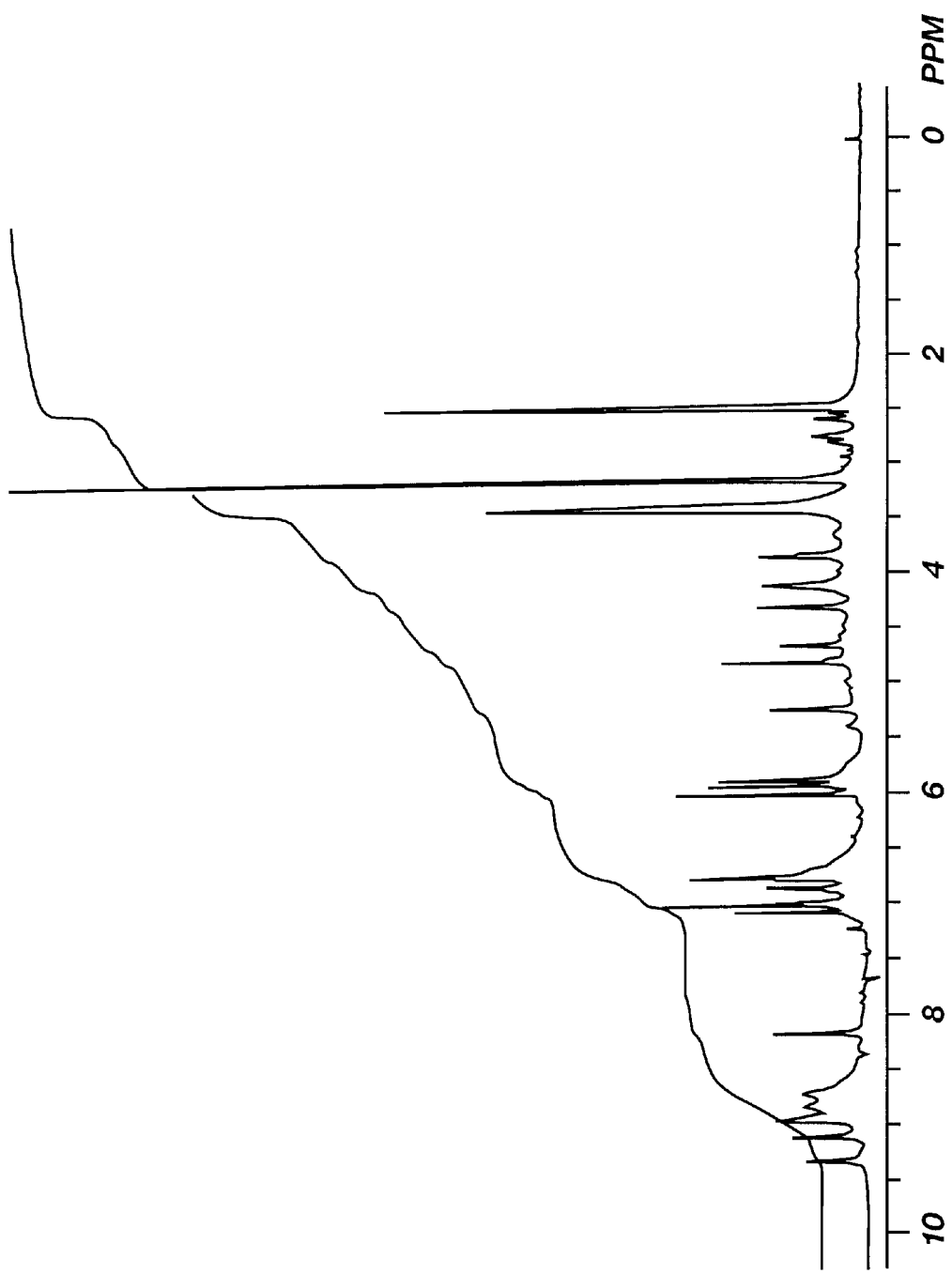
FIG. 8 is a chart depicting a $^1$H-NMR spectrum of the isolated active material isolated as per FIG. 5.

FIG. 8 depicts a $^1$H-NMR scan of product from the aforementioned step, also in $d_6$-DMSO.

Figure 9A:
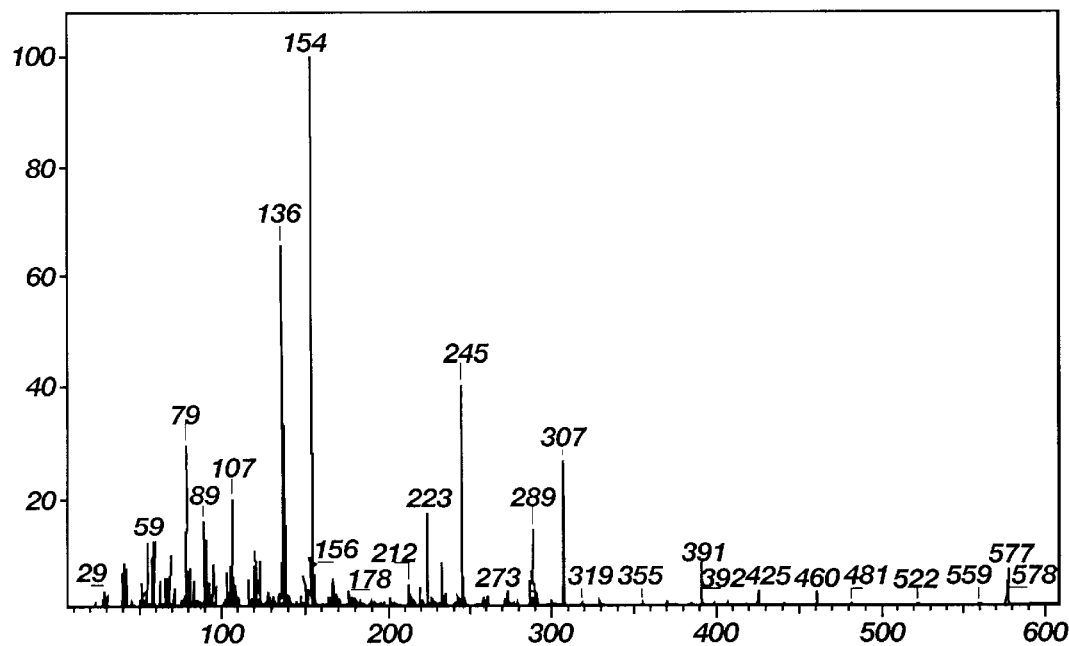
FIG. 9A & 9B are charts depicting mass spectrograms of the isolated active material isolated as per FIG. 5.
Figure 9B:
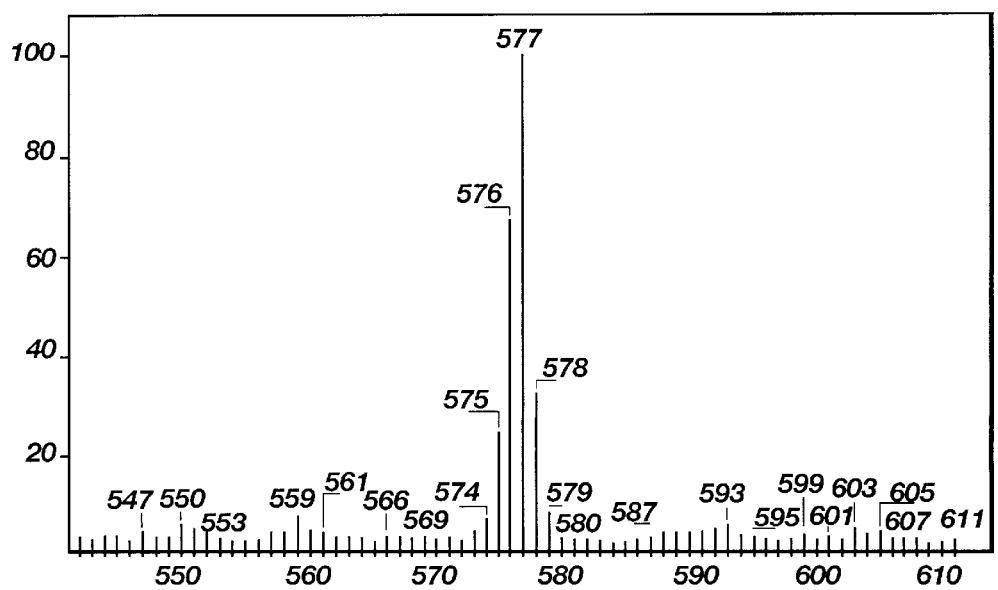

FIG. 9A and 9B depict mass spectrograms of product from the aforementioned step, dissolved in 3-nitrobenzyl alcohol with DMSO.

From this data, it is evident that the product from the aforementioned step has many of the characteristics of a proanthocyanidin. In addition, it is further believed that in addition to the dimer, the material in the region 1410 beneath the peak 1408 of the HPLC of FIG. 6C includes polymeric proanthocyanidins and that these polymeric proanthocyanidins are highly active as well polymeric proanthocyanidins.

Proanthocyanidin oligomers or polymers useful for present anti-microbial methods are included of monomeric units of leucoanthocyandins. Leucoanthocyandins are generally monomeric flavonoids which include catechins, epicatechins, gallocatechins, galloepicatechins, flavonols, and flavan-3,4-diols leucocyanidins and anthocyanidins. The proanthocyanidin polymers have 2 to 30 flavonoid units.

In addition, it was found that crystal formation occurred upon storage of the LH-20 30% MeOH eluate under nitrogen for periods of from one to several weeks or more. Apparently, under slow purging of the nitrogen atmosphere, the eluate (generally 1–2 ml volume) becomes sufficiently concentrated that the purified active compound spontaneously crystallizes; such behavior is known for various polyphenolic compounds. Crystals grown from the 30% methanol eluate have been analyzed by X-ray crystallographic methods. From the data, it is evident that the product from the 20:80 mixture step has many characteristics of a proanthocyanidin. In addition, it is further believed that in addition to the dimer, the material in the region 1410 beneath the peak 1408 of the HPLC of FIGS. 6D and 6E includes polymeric proanthocyanidins of various chain lengths up to 5000 Daltons molecular weight and that these are highly active as well.

Certain other compounds present in the extract have been further identified as having anti-adhesion activity, and in some cases these compounds have been partially purified. These include leukocyanidins/leukodelphinidins and flavonol pyranosides. Leukocyanidins/leukodelphinidins and flavonol pyranosides include a general structure of a catechin molecule (Merck Index # 1908); epicatechin differs from catechin in the orientation of the hydroxyl at position 3, and the hydrogen at position 2 of the phenol group.

In general, compounds having a ring system, wherein the ring B may include oxygen at position 1, position 4, or both, and having a pyranoside as $R^2$, have anti-adhesion activity. The ring B is further unsaturated except for the C=C bond shared with ring A. Evidence for the necessity of the unsaturation of ring B and the necessity of $R^2$ being a pyranoside is as follows. Leucoanthocyanins (exemplified as leucocyanin and leucodelphinin) are colorless compounds having the catechin or epicatechin ring structure with an unsaturated ring B and a pyranoside in the $R^2$ position. Upon treatment of leucocyanins by heating in aqueous acid solution, the O-$R^2$ carbohydrate linkage is hydrolyzed and the result is a cyanidin (or delphinidin), wherein ring B is fully saturated and gives a characteristic red color. The material in certain HPLC peaks of the Vaccinium extract which absorb at 280 nm and are found to contain anti-adhesion activity, is initially colorless. Upon treatment with heat and aqueous acid, carbohydrate moieties are released, red color appears in the fraction at the characteristic anthocyanin absorbance wavelength of 512 nm, and the activity in the material is lost.

Further, quercetin and myricetin, which both share the catechin or epicatechin-like nucleus with leucocyanins but have $R^2$=H or OH, have been tested in the anti-adhesion assay and show no activity. However, myricetin-3-pyranoside isolated from Vaccinium species does have anti-adhesion activity. Further, as described previously herein, one of the anti-adhesion assays described herein compares the ability of a substance to inhibit binding relative to mannose inhibition of such adhesion, and it is therefore believed that a carbohydrate moiety is involved in conferring anti-adhesion activity.

Based on the above observations, applicants conclude that wherein X=C or O; $R^1$=H or OH, $R^2$=H, OH, pyranoside, a pyranoside chain, or galloyl; $R^3$=H or OH; $R^4$= catechin, epicatechin, or procyanidin polymer; all possess some degree of inhibitory effect on adherence of microbes to cell surfaces. Further, the microbes whose adherence to cells is interfered with include bacteria, yeast and possibly viruses which bind to cell surfaces as a first step in infecting them.

The invention is described with reference to specific embodiments, plant species and parts, buffers and chemical procedures and the like. However, it will be recognized by those skilled in the art that various substitutions can be made without departing from the spirit and scope of the invention. In particular, it is known that polyphenols including flavonoids and anthocyanins can be isolated and/or partially purified from plant materials by a number of different methods. It will further be recognized that these alternate methods, and consequent changes in other steps of the method including removal of sugars, of various solvents, and of anthocyanins from a composition including partially purified polyphenols, fall within the scope of the present invented Vaccinium extract.

What is claimed is:

1. A proanthocyanidin composition having a peak located at about 95 ppm on a $^{13}$C NMR, said proanthocyanidin composition consisting essentially of proanthocyanidin compounds having an average of from at least four to about seven epicatechin flavanoid units, wherein at least two of said units are linked together by an A-type interflavanoid linkage by bonds between C4 and C8 and between the C2 and the oxygen of C7 of the units and the remainder of the units are linked to each other by a B-type interflavanoid bond between C4 and C8 or between C4 and C6 of the units.

2. The proanthocyanidin composition of claim 1, wherein said proanthocyanidin compounds consist of an average of four, five or six epicatechin flavanoid units.

3. A pharmaceutical composition comprising the proanthocyanidin composition of claim 1 and a pharmaceutically acceptable carrier.

4. A food composition comprising a consumable carrier in admixture with the proanthocyanidin composition of claim 2.

5. The food composition of claim 4, wherein said consumable carrier is animal feed.

6. The food composition of claim 4 wherein said consumable carrier is a consumable food product.

7. The composition of claim 6, wherein said consumable food product is a cranberry-containing food product.

8. The composition of claim 7, wherein said cranberry-containing food product is a dried cranberry, a sweetened and dried cranberry, a flavored fruit piece, a sauce, a jelly, a relish, juice, wine or a cranberry juice-containing product.

9. The composition of claim 7, wherein said consumable food product is a beverage.

10. The composition of claims 9, wherein said beverage comprises cranberry juice, unpasteurized juice or pasteurized juice.

11. A food composition comprising a consumable carrier in admixture with the proanthocyanidin composition of claim 1, wherein the proanthocyanidin agglutinaton of P-type *E. coli*.

* * * * *